United States Patent
Cornelis et al.

(10) Patent No.: US 10,449,204 B2
(45) Date of Patent: Oct. 22, 2019

(54) USE OF VANADIUM COMPOUNDS FOR MAINTAINING NORMAGLYCEMIA IN A MAMMAL

(75) Inventors: Hendrik Jan Cornelis, Wespelaar (BE); Lekhram Changoer, Ijsselstein (NL)

(73) Assignee: CFM PHARMA HOLDING BV, Vianen (NL)

( * ) Notice: Subject to any disclaimer, the term of this patent is extended or adjusted under 35 U.S.C. 154(b) by 1110 days.

(21) Appl. No.: 14/003,729

(22) PCT Filed: Mar. 6, 2012

(86) PCT No.: PCT/NL2012/050136
§ 371 (c)(1),
(2), (4) Date: Nov. 11, 2013

(87) PCT Pub. No.: WO2012/121596
PCT Pub. Date: Sep. 13, 2012

(65) Prior Publication Data
US 2014/0072647 A1    Mar. 13, 2014

Related U.S. Application Data

(60) Provisional application No. 61/449,787, filed on Mar. 7, 2011.

(51) Int. Cl.
| | | |
|---|---|---|
| *A61K 33/00* | (2006.01) | |
| *A61K 33/06* | (2006.01) | |
| *A61K 31/7135* | (2006.01) | |
| *A61K 31/555* | (2006.01) | |
| *A61K 31/28* | (2006.01) | |
| *A61K 31/30* | (2006.01) | |
| *A61K 31/59* | (2006.01) | |
| *A61K 33/04* | (2006.01) | |
| *A61K 33/14* | (2006.01) | |
| *A61K 33/24* | (2019.01) | |
| *A61K 33/34* | (2006.01) | |
| *A61K 45/06* | (2006.01) | |
| *A61K 38/28* | (2006.01) | |
| *A23L 33/16* | (2016.01) | |

(52) U.S. Cl.
CPC ............ *A61K 31/555* (2013.01); *A23L 33/16* (2016.08); *A61K 31/28* (2013.01); *A61K 31/30* (2013.01); *A61K 31/59* (2013.01); *A61K 33/00* (2013.01); *A61K 33/04* (2013.01); *A61K 33/06* (2013.01); *A61K 33/14* (2013.01); *A61K 33/24* (2013.01); *A61K 33/34* (2013.01); *A61K 38/28* (2013.01); *A61K 45/06* (2013.01); *A23V 2002/00* (2013.01)

(58) Field of Classification Search
CPC ..... A61K 33/00; A61K 33/06; A61K 31/7135
USPC ...................... 424/646, 643, 615
See application file for complete search history.

(56) References Cited

U.S. PATENT DOCUMENTS

| | | |
|---|---|---|
| 5,300,496 A | 4/1994 | McNeill et al. |
| 5,527,790 A | 6/1996 | McNeill et al. |
| 5,620,967 A | 4/1997 | McNeill et al. |
| 5,866,563 A | 2/1999 | McNeil et al. |
| 5,885,980 A * | 3/1999 | Gutierrez ............... A61K 31/64 514/186 |
| 5,888,993 A | 3/1999 | McNeil et al. |
| 6,287,586 B1 | 9/2001 | Orvig et al. |
| 6,579,540 B1 * | 6/2003 | Gho ...................... A61K 33/24 424/646 |
| 6,852,760 B1 | 2/2005 | Fine et al. |
| 2005/0171503 A1 | 8/2005 | Van Den Berghe et al. |
| 2011/0027348 A1 * | 2/2011 | Feher .................... A61K 35/74 424/450 |

FOREIGN PATENT DOCUMENTS

WO    WO-99/12875 A1    3/1999

OTHER PUBLICATIONS

Mehta, Ravindra L. "Glycemic Control and Critical Illness: Is the Kidney Involved?" Journal American Soc. Nephrol: 18: 2623-2627, 2007).*
O'Connell, Belinda S., MS, RD. LD, "Select Vitamins and Minerals in the Management of Diabetes", Diabetes Spectrum, vol. 14, No. 3, 2001).*
Meyerovitch et al. "Oral Administration of Vanadate Normalizes Blood Glucose Levels in Streptozotocin-treated Rats", The Journal of Biological Chemistry, 1987, Vo., 262, No. 14, pp. 6658-6662).*
"The World in Medicine", American Medical Association, 2009.*
McNeill et al., "Bis(maltolato)oxovanadium(IV) is a potent insulin mimic", Journal of Medicinal Chemistry, 1992, vol. 35, No. 8, pp. 1489-1491.
Morimatsu et al., "The impact of intensive metabolic management in intensive care", Japanese Journal of Intensive Care Medicine, 2007, vol. 31, No. 7, pp. 527-534, with English abstract.
Thompson et al., "Insulin-mimetic vanadium complexes", Revista Portuguesa de Quimica, 1997, vol. 4, pp. 3-10.
Capes, et al. "Stress Hyperglycemia and Prognosis of Stroke in Nondiabetic and Diabetic Patients: A Systematic Overview", Stroke, 2001, vol. 32, pp. 2426-2432.
Cros, et al. "Long-term antidiabetic activity of vanadyl after treatment withdrawal: Restoration of insulin secretion?", Molecular and Cellular Biochemistry, 1995, vol. 153, pp. 191-195.
International Search Report in PCT/NL2012/050136 dated Jul. 30, 2012.
McCullough, P. "Cardiorenal Syndromes: Pathophysiology to Prevention", International Journal of Nephrology, 2011, Article ID 762590, pp. 1-10.
Van Den Berghe, et al. "Intensive Insulin Therapy in Critically Ill Patients", The New England Journal of Medicine, Nov. 8, 2001, vol. 345, No. 19, pp. 1359-1367.

* cited by examiner

*Primary Examiner* — Michael Barker
*Assistant Examiner* — Deborah A Davis
(74) *Attorney, Agent, or Firm* — Gilberto M. Villacorts; Sunit Talapatra; Foley & Lardner LLP

(57) ABSTRACT

The present invention relates to a method for maintaining normoglycemia in a mammal in need thereof, preferably a critically ill patient suffering from acute stress, and to a method for preventing or limiting renal ischemia-reperfusion (I/R) in a mammal, preferably in a critically ill patient suffering from acute stress.

11 Claims, 7 Drawing Sheets

USE OF VANADIUM COMPOUNDS FOR MAINTAINING NORMAGLYCEMIA IN A MAMMAL

CROSS-REFERENCE TO RELATED APPLICATIONS

This application is the National Phase of International Patent Application No. PCT/NL2012/050136, filed Mar. 6, 2012, published as WO 2012/121596, which claims priority to U.S. Provisional Application No. 61/449,787, filed Mar. 7, 2011. The contents of these applications are herein incorporated by reference in their entirety.

FIELD OF THE INVENTION

The present invention relates to a method for maintaining normoglycemia in a mammal in need thereof, preferably a critically ill patient suffering from acute stress. The present invention further relates to a method for preventing or limiting renal ischemia-reperfusion (I/R) in a mammal in need thereof, preferably a critically ill patient suffering from acute stress. The present invention also relates to a method for the prevention, limitation or treatment of cardio-renal disorders in a mammal in need thereof, preferably a critically ill patient suffering from acute stress. The present invention further relates to a pharmaceutical composition for use in maintaining normoglycemia in a critically ill patient suffering from acute stress.

BACKGROUND OF THE INVENTION

A high proportion of patients suffering from an acute stress, e.g. a stroke or a myocardial infarction, develops hyperglycemia, even if these patients have not earlier been diagnosed for diabetes. Such stress-induced hyperglycemia is associated with a high risk of mortality after both stroke and myocardial infarction. Moreover, stress-induced hyperglycemia may be a risk factor for brain damage (cf. Sarah E. Capes et al., Stroke 2001, 32, page 2426).

Additionally, hyperglycemia and insulin resistance are common in critically ill patients in general, even when glucose homeostasis has previously been normal (cf. US 2005/171503, incorporated by reference).

G. Van den Berghe et al. (N. Engl. J. Med. 2001, 345, 1359-1367) found that even moderate hyperglycemia in diabetic as well as in non-diabetic critically ill patients is directly or indirectly harmful to vital organs and systems. Intensive insulin therapy reduced overall ICU (Intensive Care Unit) mortality from 8% to 4.6%, and from 20.2% to 10.6% among patients requiring more than five days intensive care. The intensive insulin therapy also significantly reduced blood stream infections, prolonged inflammation, acute renal failure, critical illness polyneuropathy and transfusion requirements. Hence, strict maintenance of normoglycemia with intensive insulin therapy reduces intensive care and hospital mortality and morbidity of critically ill adult patients in an ICU.

However, intensive insulin therapy requires knowledge of patient blood sugar levels which involves frequently obtaining (capillary) blood samples. This necessitates considerable nurse or technician time and many patients, especially non-diabetics, find repeated blood sampling objectionable. Furthermore, intermittent blood samples may not be done often enough to give an accurate picture of blood sugar levels. Other disadvantages of intensive insulin therapy include: an increase in hypoglycaemia risk (it is known in the art that hypoglycaemia increases the risk of myocardial infarction and ventricular arrhythmia; cf. US 2005/171503, incorporated by reference), sedation can mask hypoglycaemia and differences in opinions of when to introduce insulin and in which patients to apply the protocol.

Hence, although insulin therapy has certainly advantages for critically ill patients as is discussed above, there is still a need in the art to provide a method for controlling insulin administration to critically ill patients, in particular critically ill patients suffering from acute stress.

Acute renal failure (ARF) is a clinical syndrome characterized by rapid deterioration of renal function that occurs within days. ARF is frequently caused by acute tubular necrosis (ATN), which results from ischemic and/or nephrotoxic insults. In the general world population, about 200 cases of severe ARF per million population occur annually. Several drugs, e.g. anti-oxidants, calcium channel blockers, diuretics, vasoactive substances, growth factors, and anti-inflammatory agents, have been investigated on their efficacy in clinical trials but have been found of little or no clinical use.

U.S. Pat. Nos. 5,300,496, 5,527,790, 5,620,967, 5,866,563 and 5,888,993, all incorporated by reference, disclose the use of vanadium compounds in the treatment of diabetes mellitus, hypertension, obesity and similar conditions related to chronically enhanced blood sugar levels.

U.S. Pat. No. 5,885,980, incorporated by reference, discloses a pharmaceutical composition for the treatment of diabetes, said pharmaceutical composition comprising a $VO^{2+}$ generating compound and micronized glyburide. Example 5 of U.S. Pat. No. 5,885,980 discloses the treatment of a type I diabetic female patient who was hospitalized in an ICU for chronic hyperglycemia with a combination of insulin, vanadyl sulfate and glynase, an anti-diabetic drug of the sulfonylureum type which is more commonly used for the treatment of type II diabetes. However, glynase may cause hypoglycemia and a hypoglycaemia defined as blood glucose below 0.3 mM/l is to increases the risk of myocardial infarction and ventricular arrhythmia (cf. US 2005/171503).

U.S. Pat. No. 6,287,586, incorporated by reference, discloses a pharmaceutical composition of particular vanadium biguanide complexes for the treatment of hyperglycemia and related disorders.

U.S. Pat. No. 6,579,540, incorporated by reference, discloses the use of physiologically acceptable vanadium compounds for the prophylactic treatment of secondary injury of tissue, wherein said secondary injury is the result of a primary injury and wherein the primary injury is caused by a trauma, e.g. reperfusion after ischemia (infarction). U.S. Pat. No. 6,579,540 does therefore not disclose the use of the physiologically acceptable vanadium compounds in the treatment of hyperglycemia or renal ischemia-reperfusion in critically ill patients.

U.S. Pat. No. 6,852,760, incorporated by reference, discloses the use of a combination of a sulfonyl ureum compound, a biologically available source of chromium and a biologically available source of vanadium for the treatment of diabetes.

Consequently, the use of vanadium compounds in controlling hyperglycemia in diabetic patients is known in the art. However, diabetes is a chronic disease. Critically ill patients are, however, hospitalized for a relatively short period of time, in particular one to several days, and in particular in an intensive care unit (ICU). Hence, diabetic patients are a different class of patients than critically ill patients.

P. A. McCullough, Int. J. Nephrol., Volume 2011, Article ID 762590 (doi: 10.4061/2011/762590) suggest that there is an interrelationship between cardiovascular disorders and renal disorders. This relationship is referred to as "cardio-renal"-disorders.

Currently, contrast-induced, preferably radio-contrast-induced nephropathy is treated with N-acetylcysteine.

SUMMARY OF THE INVENTION

The present invention relates to a method for maintaining normoglycemia in a mammal in need thereof, preferably a critically ill patient suffering from acute stress, wherein a pharmaceutical composition comprising a physiologically acceptable organic and/or inorganic vanadium compound or complex is administered to said mammal.

The present invention also relates to a method for preventing or limiting renal ischemia-reperfusion (I/R) in a mammal in need thereof, preferably a critically ill patient suffering from acute stress, wherein a pharmaceutical composition comprising a physiologically acceptable organic and/or inorganic vanadium compound or complex is administered to said mammal.

The present invention also relates to a method for the prevention, limitation or treatment of cardio-renal disorders in a mammal in need thereof, preferably a critically ill patient suffering from acute stress, wherein a pharmaceutical composition comprising a physiologically acceptable organic and/or inorganic vanadium compound or complex is administered to said mammal.

The present invention further relates to a pharmaceutical composition for use in maintaining normoglycemia in a critically ill patient suffering from acute stress.

The present invention further relates to a pharmaceutical composition comprising a physiologically acceptable organic and/or inorganic vanadium compound or complex for use in preventing or limiting renal ischemia-reperfusion (I/R) in a critically ill patient suffering from acute stress.

The present invention further relates to a pharmaceutical composition comprising a physiologically acceptable organic vanadium compound or complex, a pharmaceutically acceptable carrier, and a second ingredient, said second ingredient being selected from the group of magnesium, fish oil, potassium, copper, selenium, vitamin D, vitamin E, chromium, and mixtures thereof.

The present invention also relates to a pharmaceutical composition comprising a physiologically acceptable organic and/or inorganic vanadium compound or complex for use in preventing or treating contrast-induced nephropathy in a mammal in need thereof.

The present invention further relates to a pharmaceutical composition comprising a physiologically acceptable organic and/or inorganic vanadium compound or complex for use in preventing, limiting or treating of cardio-renal disorders in a mammal in need thereof.

DETAILED DESCRIPTION OF THE INVENTION

Definitions

Figure 1:
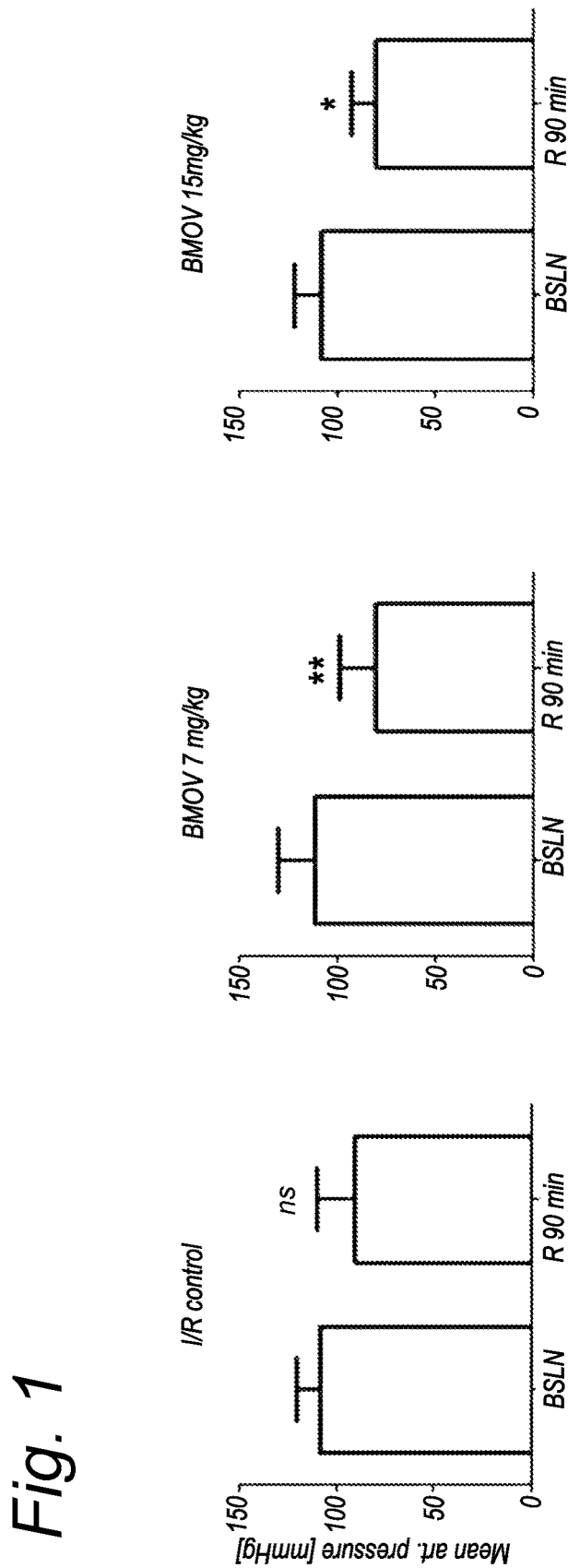
FIG. 1 shows the mean arterial (art.) pressure at baseline (BSLN) and after 30 min of ischemia and 90 min of reperfusion (R 90 min).

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

In this document, the term "critically ill patient" refers to a group of patients who are hospitalized for a relatively short period of time, in particular one to several days, more in particular one to seven days, in an a intensive care unit (ICU). Preferably, the term "critically ill patient" refers to this group of patients who are suffering from acute stress, in particular acute renal failure (ARF), acute renal insufficiency (ACI) or both. It is suggested that renal ischemia-reperfusion (I/R) to the kidney, which can occur as a result of or can occur during e.g. cardiac or vascular surgery, kidney transplant, elective aortic aneurysm repair and shock (for example cardiogenic, hemorrhagic or septic shock), affects renal microcirculation which prevents proper tissue reperfusion. This may lead to undesired effects such as renal hypoxia, oxidative stress and irreversible damage with organ failure.

The term "cardio-renal"-disorders" is defined as disorders of organs like the heart and the kidney whereby acute or chronic dysfunction in one organ may induce acute or chronic dysfunction in the other organ. Several possible pathophysiologic mechanisms for each disorder have been proposed.

The present invention therefore relates to a method for maintaining normoglycemia in a mammal in need thereof, preferably a critically ill patient suffering from acute stress, wherein a pharmaceutical composition comprising a physiologically acceptable organic and/or inorganic vanadium compound or complex is administered to said mammal.

The present invention further relates to a method for preventing or limiting renal ischemia-reperfusion (I/R) in a mammal in need thereof, preferably a critically ill patient suffering from acute stress, wherein a pharmaceutical composition comprising a physiologically acceptable organic and/or inorganic vanadium compound or complex is administered to said mammal. More in particular, the present invention further relates to a method for preventing or limiting renal ischemia-reperfusion (I/R) in a kidney of a mammal in need thereof, preferably a critically ill patient suffering from acute stress, wherein a pharmaceutical composition comprising a physiologically acceptable organic and/or inorganic vanadium compound or complex is administered to said mammal.

It has surprisingly been found that the pharmaceutical composition according to the present invention significantly increases microvascular oxygenation in the renal cortex and in the medulla of a mammal in need thereof, preferably a critically ill patient, wherein this microvascular oxygenation was earlier reduced by an I/R injury.

It has also surprisingly been found that the pharmaceutical composition according to the present invention increases renal oxygen utilization efficiency in a mammal in need thereof, preferably in a critically ill patient, which was earlier reduced by an I/R injury.

In addition, it has surprisingly been found that the pharmaceutical composition according to the present invention significantly decreases inflammation activation in a mammal in need thereof, preferably in a critically ill patient, caused by an earlier I/R injury.

Furthermore, it has surprisingly been found that the pharmaceutical composition according to the present invention significantly decreases renal injury in a mammal in need thereof, preferably in a critically ill patient, caused by an earlier I/R injury.

The present invention further relates to a method for preventing or treating contrast-induced, preferably radio-contrast-induced nephropathy which is a form of acute renal failure (ARF) in a mammal in need thereof, wherein a pharmaceutical composition comprising a physiologically acceptable organic and/or inorganic vanadium compound or complex is administered to said mammal.

According to an embodiment of the present invention, the critically ill patient is non-diabetic.

According to the present invention, it is preferred that the acute stress is induced by an injury, an insult, a trauma, a medical treatment, an infection, a stroke, vascular or coronary bypass surgery, shock, preferably cardiogenic, hemorrhagic or septic shock, or a treatment of myocardial infarction.

Preferably, the blood glucose levels are maintained in the mammal, preferably the critically ill patient, between about 80 and about 110 mg/dl. (about 4.4 to about 6.1 mmol/l). Preferably, the blood glucose levels are maintained between about 85 and about 100 mg/dl.

According to an embodiment, the pharmaceutical composition according to the present invention which comprises the physiologically acceptable organic and/or inorganic vanadium compound or complex is administered parenterally. According to another embodiment of the present invention, the pharmaceutical composition is administered intravenously.

Since the critically ill patient is hospitalised in an a intensive care unit (ICU), the methods according to the present invention are carried out for one to seven days, preferably for one to six days, more preferably for one to five days, even more preferably for one to four days, yet even more preferably for one to three days, yet even more preferably for one to two days and in particular for one day only.

According to an embodiment of the present invention, it is preferred that insulin or an insulin analogue is co-administered to the mammal, preferably the critically ill patient.

According to another embodiment of the present invention, an anti-arrhythmic drug is co-administered to the mammal, preferably the critically ill patient.

According to yet another embodiment of the present invention, a nutritional supplement is co-administered to the mammal, preferably the critically ill patient. Here it is preferred that the nutritional supplement is selected from the group of magnesium, fish oil, potassium, copper, selenium, vitamin D, Vitamin E, and mixtures thereof.

According to a preferred embodiment of the present invention, the physiologically acceptable organic and/or inorganic vanadium compound or complex is bis(maltolato)oxovanadium(IV) (also known as BMOV). BMOV and its synthesis are known in the art (CAS 38213-69-3).

The present invention therefore also relates to pharmaceutical compositions comprising a physiologically acceptable organic and/or inorganic vanadium compound or complex, a pharmaceutically acceptable carrier, and a second ingredient, said second ingredient being selected from the group of magnesium, fish oil, potassium, copper, selenium, vitamin D and mixtures thereof.

The present invention further relates to a pharmaceutical composition comprising a physiologically acceptable organic and/or inorganic vanadium compound or complex for use in maintaining normoglycemia in a critically ill patient suffering from acute stress.

It is preferred that the critically ill patient is non-diabetic as is described above.

Preferably, the acute stress is induced by an injury, an insult, a trauma, a medical treatment, an infection, a stroke, coronary bypass surgery or a treatment of myocardial infarction.

According to the present invention, it is preferred that the pharmaceutical composition is administered in sufficient amounts so that blood glucose levels are maintained between about 80 and about 110 mg/dl. (about 4.4 to about 6.1 mmol/l), preferably between about 85 and about 100 mg/dl.

Preferably, the pharmaceutical composition according to the present invention is administered parenterally or intravenously.

Preferably, the pharmaceutical composition according to the present invention is administered for one to seven days, preferably for one to six days, more preferably for one to five days, even more preferably for one to four days, yet even more preferably for one to three days, yet even more preferably for one to two days and in particular for one day only.

The pharmaceutical composition according to the present invention may further comprise insulin or an insulin analogue, an anti-arrhythmic drug, a nutritional supplement, or a combination thereof. Preferably, the nutritional supplement is selected from the group of magnesium, fish oil, potassium, copper, selenium, vitamin D, vitamin E, chromium and mixtures thereof.

The present invention further relates to a pharmaceutical composition comprising a physiologically acceptable organic and/or inorganic vanadium compound or complex for use in preventing or limiting renal ischemia-reperfusion (I/R) in a critically ill patient suffering from acute stress.

The present invention further relates to a pharmaceutical composition comprising a physiologically acceptable organic vanadium compound or complex, a pharmaceutically acceptable carrier, and a second ingredient, said second ingredient being selected from the group of magnesium, fish oil, potassium, copper, selenium, vitamin D, vitamin E, chromium, and mixtures thereof.

The present invention also relates to a pharmaceutical composition comprising a physiologically acceptable organic and/or inorganic vanadium compound or complex for use in preventing or treating contrast-induced nephropathy in a mammal in need thereof. Preferably, the mammal is a critically ill patient suffering from acute stress.

The present invention further relates to a pharmaceutical composition comprising a physiologically acceptable organic and/or inorganic vanadium compound or complex for use in preventing, limiting or treating of cardio-renal disorders in a mammal in need thereof. Preferably, the mammal is a critically ill patient suffering from acute stress.

EXAMPLES

Materials and Methods
Animals

This study protocol was reviewed and approved by the institutional Animal Experimentation Committee of the Academic Medical Center of the University of Amsterdam. The handling and care of the animals was in accordance with the Institute for Laboratory Animal Research Guide for Care and Use of Laboratory Animals.

Thirty two male Wistar rats (Harlan Netherlands BV, Horst, The Netherlands) with a mean body weight of 280±30 grams were used in this study. The animals were quarantined prior to start of the investigation for 1 week to permit acclimatization to their new environment and were housed in pairs in conventional cages in a light-controlled room kept at 22±1° C. with a relative humidity of 55±10%. All animals received standard laboratory rat chow and water for consumption ad libitum.

Surgical Preparation

All animals were initially anesthetized with a mixture of ketamine (Nimatek, Eurovet Animal Health BV, Bladel, The Netherlands; 90 mg/kg), dexmedetomidine (Dexdomitor, Pfizer Animal Health BV, Capelle aan den IJssel, The Netherlands; 0.5 mg/kg), and atropine sulfate (Centrafarm BV, Etten-Leur, The Netherlands; 0.05 mg/kg) by intraperitoneal injection. Once anesthetized, the area between the thoracic manubrium and chin and the left flank covering the left kidney were shaved and cleaned prior to initiating the surgical procedure. During the remainder of the surgical preparation and experimental procedures, anesthesia was maintained via tracheotomy and mechanical ventilation with an inspired oxygen fraction ($FiO_2$) of 0.4. Body temperature was maintained at 37±0.5° C. during the entire experiment. The ventilator settings were adjusted to maintain an arterial $pCO_2$ between 35 and 40 MmHg.

For drug and fluid administration and hemodynamic monitoring, three vessels were cannulated with polyethylene catheters (outer diameter=0.9 mm; Braun, Melsungen, Germany). A catheter in the right carotid artery was connected to a pressure transducer to monitor arterial blood pressure and heart rate. The right jugular vein was cannulated for continuous infusion of Ringer's lactate (Baxter, Utrecht, The Netherlands) at a rate of 15 ml/kg/hr. The femoral artery was cannulated for withdrawing blood samples for blood gas analysis. Animals were kept under general anesthesia during all experiments and received continuous intravenous diluted ketamine or analgesic drug infusions. The left kidney was exposed, decapsulated, and immobilized in a Lucite (i.e. poly (methyl methacrylate); PMMA) custom made kidney cup via a ~4 cm incision on the left flank. The renal artery and vein were carefully separated to preserve the surrounding nerves and adrenal gland. A perivascular ultrasonic transient time flow probe (type 0.7 RB; Transonic Systems, Ithaca, N.Y., USA) was placed around the left renal artery and connected to a flow meter (T206; Transonic Systems, Ithaca, N.Y., USA) to allow continuous measurement of renal blood flow (RBF). The left ureter was isolated, ligated, and cannulated with a polyethylene catheter (outer diameter=0.9 mm; Braun, Melsungen, Germany) for urine collection. A small piece of aluminum foil (10×10 mm) was placed on the dorsal site of the renal vein to prevent contribution of juxtaposed and underlying tissues from interfering with the phosphorescence signal in the venous pO2 measurement. After the surgical protocol (~60 min), one optical fiber was placed 1 mm above the decapsulated kidney and another optical fiber 1 mm above the renal vein to measure oxygenation using a phosphorescence lifetime technique (20). Oxyphor G2 (Oxygen Enterprises, Philadelphia, Pa., USA; 6 mg/kg) was subsequently infused intravenously for 5 min, followed by 30 min of stabilization time.

The operation field was covered with a humidified gauze compress throughout the entire experiment to prevent drying of the exposed tissues in the surgical field. The phosphorescence lifetime measurements have been described in more details elsewhere (20). The experiment was terminated by infusion of 1 ml of 3 M potassium chloride. Finally, the kidney was removed, weighed, and processed for histological evaluation. The correct placements of the catheters were also checked postmortem.

Experimental Protocol

After completion of the surgical preparation followed by 30 min of stabilization time, each animal was randomly allocated into the following groups: BMOV 7 mg/kg (n=6); BMOV 15 mg/kg; (n=6), I/R control (n=8), and time control (n=3). BMOV infusion was initiated 15 minutes prior to the 30 minutes ischemia period and infusion was continued through the whole experiment.

Hemodynamic and Blood Gas Parameters

Mean arterial pressure (MAP) was continuously monitored from the right common carotid artery. Additionally, the renal artery blood flow [RBF; ml/min] was recorded continuously using a transit-time ultrasound flow probe (type 0.7 RB; Transonic Systems Inc., Ithaca, N.Y.). Arterial blood samples (0.5 ml) were taken from the carotid artery at baseline (BSLN) and 90 min after ischemia (R 90 min). The blood samples were replaced by the same volume of HES130/0.4 (Voluven®, 6% HES 130/0.4; Fresenius Kabi Nederland B.V., Schelle, Belgium). The samples were used for determination of blood gas values (ABL505 blood gas analyzer; Radiometer, Copenhagen, Denmark), as well as for determination of the hemoglobin concentration, hemoglobin oxygen saturation, and sodium and potassium concentrations (OSM 3; Radiometer).

Renal Microvascular and Venous $pO_2$

Oxygen-quenched phosphorescent lifetimes of a systemically infused albumin-targeted (and therefore circulation confined) phosphorescent dye (Oxyphor G2; Oxygen Enterprises, Ltd. Philadelphia, Pa., USA) was measured using a dual-wavelength timedomain phosphorimeter, and used to detect alterations in microvascular and venous $pO_2$ ($\mu pO_2$). Oxyphor G2 (a two-layer glutamate dendrimer of tetra-(4-carboxy-phenyl)benzoporphyrin) has two excitation peaks ($\lambda$excitation1=440 nm, excitation2=632 nm) and one emission peak ($\lambda$emission=800 nm), which allows simultaneous lifetime measurements in the kidney cortex and the outer medulla due to different optical penetration depths of the excitation light. For the measurement of renal venous $pO_2$ ($PrvO_2$) a mono-wavelength frequency-domain phosphorimeter was used. The correlation between the measured lifetimes and the $pO_2$ values was given by the Stern-Volmer relation: $1/\tau=(1/\upsilon 0)+kq\,[O_2]$, where $\tau$ is the measured lifetime, $\tau 0$ is the lifetime at an oxygen concentration of zero mmHg and kq is the known quenching constant.

Renal Function

Urine samples from the left ureter were collected for analysis of urine volume and creatinine concentration. Plasma samples for analysis of creatinine concentration were obtained at the midpoint of each urine collection period. The concentrations of creatinine in urine and plasma were determined by colorimetric methods. Creatinine clearance (Clearcrea [ml/min]) was assessed as an index of the glomerular filtration rate.

Calculations of the clearance was done using the standard formula:

$$Clear_{crea}=(U_{crea} \times V)/P_{crea},$$

where $U_{crea}$ is the concentration of creatinine in urine, V is the urine volume per unit time and $P_{crea}$ is the concentration of creatinine in plasma.

Furthermore, all urine samples were analyzed for sodium ($Na^+$) concentration. Excretion fraction of $Na^+$ ($EF_{Na+}$ [%]) was used as a marker of tubular function and was calculated as follows:

$$EF_{Na+}=(U_{Na+} \times P_{crea})/(P_{Na+} \times U_{crea}) \times 100,$$

where $U_{Na+}$ is $Na^-$ concentration in urine, and $P_{Na+}$ the concentration of $Na^+$ in plasma. $Clear_{crea}$ and $EF_{Na+}$ were determined at baseline and after reperfusion.

Immunohistochemical Analysis

Kidney tissues were fixed in 4% formalin and embedded in paraffin. Kidney sections (5 μm) were deparaffinized with xylene and rehydrated with decreasing percentages of ethanol and finally with water. Antigen retrieval was accomplished by microwaving slides in citrate buffer (pH 6.0) (Thermo Scientific, AP-9003-500) for 10 min. Slides were left to cool for 20 min at room temperature and then rinsed with distilled water. Surroundings of the sections were marked with a PAP pen. The endogenous peroxidase activity was blocked with 3% $H_2O_2$ for 10 min at room temperature and later rinsed with distilled water and PBS. Blocking reagent (Lab Vision, TA-125-UB) was applied to each slide followed by 5 min incubation at room temperature in a humid chamber. Kidney sections were incubated for overnight at 4° C. with rabbit polyclonal iNOS antibody (iNOS Ab-1, Rabbit PAb, RB-1605-P, NeoMarkers Fremont, Calif.) and IL-6 (Abcam, 6672), and incubated for 1 hour at room temperature with anti-myeloperoxidase (MPO) antibodies (Myeloperoxidase Ab-1, RB-373-A, NeoMarkers Fremont, Calif.), Lipocalin 2 antibody (NGAL) (abcam 41105), polyclonal antibody to rat L-FABP (Hycult Biotect HP8010). Antibodies were diluted in a large volume of UltrAb Diluent (Thermo Scientific, TA-125-UD). The sections were washed in PBS three times for 5 min each time and then incubated for 30 min at room temperature with biotinylated goat anti-rabbit antibodies (LabVision, TP-125-BN). After slides were washed in PBS, the streptavidin peroxidase label reagent (LabVision, TS-125-HR) was applied for 30 min at room temperature in a humid chamber. The colored product was developed by incubation with AEC. The slides were counterstained with Mayer's hematoxylin (LabVision, TA-125-MH) and mounted in vision mount (Lab Vision, TA-060-UG) after being washed in distilled water. Both the intensity and the distribution of iNOS, IL-6, L-FABP, NGAL and MPO staining were scored. For each sample, a histological score (HSCORE) value was derived by summing the percentages of cells that stained at each intensity multiplied by the weighted intensity of the staining [HSCORE=S Pi (i+1), where i is the intensity score and Pi is the corresponding percentage of the cells] (Senturk et. al., 1999). We evaluated MPO reaction in the glomerulus from 240 selected glomeruli and in 240 selected peritubular areas under a light microscope at a magnification X400. We scored 1 if leukocytes could be seen in the glomerulus and 0 if not (Demirci et. al., 2006; Legrand et. al; 2009).

Statistical Analysis

Data analysis was performed using GraphPad Prism version 5.0 for Windows (GraphPad Software Inc., La Jolla, Calif., USA). All data are presented as mean±SD. Comparative analysis of parameters between groups and time points was performed by two-way analysis of variance (ANOVA) with Bonferroni post hoc tests. Differences between with a P-value of less than 0.05 were considered statistically significant. Table 1 shows the time control results. These results show that the mean arterial pressure was reduced by I/R injury, that BMOV did not affect mean arterial pressure and that the effects of BMOV were not dose-dependent.

TABLE 1

|  | BSLN | R 90 (min) | p-value |
| --- | --- | --- | --- |
| Mean art. press. | 103.5 ± 4.2 | 98.5 ± 4.5 | >0.05 |
| Renal vasc. res. | 22 ± 2 | 22 ± 2 | >0.05 |
| Renal blood flow | 4.7 ± 0.6 | 4.6 ± 0.5 | >0.05 |
| Renal $DO_2$ | 1.2 ± 0.2 | 1.2 ± 0.1 | >0.05 |
| $C\mu PO_2$ | 65 ± 7 | 60 ± 6 | >0.05 |
| $M\mu PO_2$ | 52 ± 6 | 49 ± 7 | >0.05 |
| Renal $VO_2$ | 0.13 ± 0.07 | 0.19 ± 0.06 | >0.05 |
| Urine volume | 0.0022 ± 0.0007 | 0.0020 ± 0.0007 | >0.05 |

Mean Arterial Pressure

As appears from FIG. 1, BMOV did not affect the mean arterial pressure (FIG. 1 shows the mean arterial (art.) pressure at baseline (BSLN) and after 30 min of ischemia and 90 min of reperfusion (R 90 min). nsp>0.05 (not significant), *p<0.05, p<0.01, and *p<0.001 vs BSLN).

Renal Hemodynamics and Oxygen Delivery

The data show that renal vascular resistance was not affected by I/R injury, but renal blood flow and oxygen delivery were significantly reduced. The data also show that BMOV did not affect renal blood flow and oxygen delivery and that the effects of BMOV were not dose-dependent.

Figure 2:
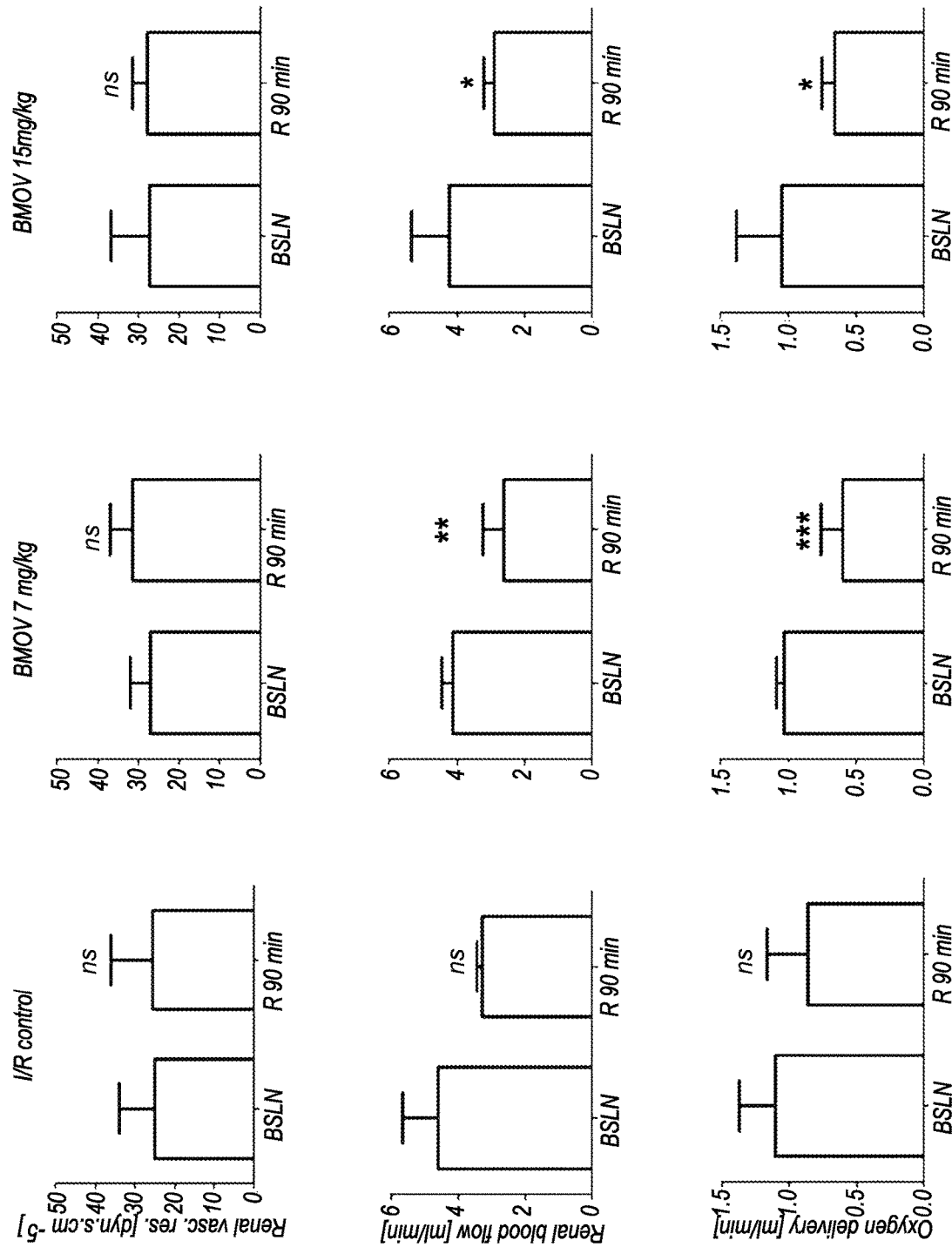
FIG. 2 shows renal vascular resistance (vasc. res.) (upper row), renal blood flow (middle row), and renal oxygen delivery (lower row) at baseline (BSLN) and after 30 min of ischemia and 90 min of reperfusion (R 90 min).

As appears from FIG. 2, BMOV did not affect renal hemodynamics and oxygen delivery (FIG. 2 shows renal vascular resistance (vasc. res.) (upper row), renal blood flow (middle row), and renal oxygen delivery (lower row) at baseline (BSLN) and after 30 min of ischemia and 90 min of reperfusion (R 90 min). nsp>0.05 (not significant), *p<0.05, p<0.01, and *p<0.001 vs BSLN).

Renal Microvascular Oxygenation

The data show that microvascular oxygenation in the renal cortex and medulla were significantly reduced by I/R injury. The data also show that BMOV significantly increased microvascular oxygenation in the renal cortex and medulla and that the effects of BMOV were not dose-dependent.

Figure 3:
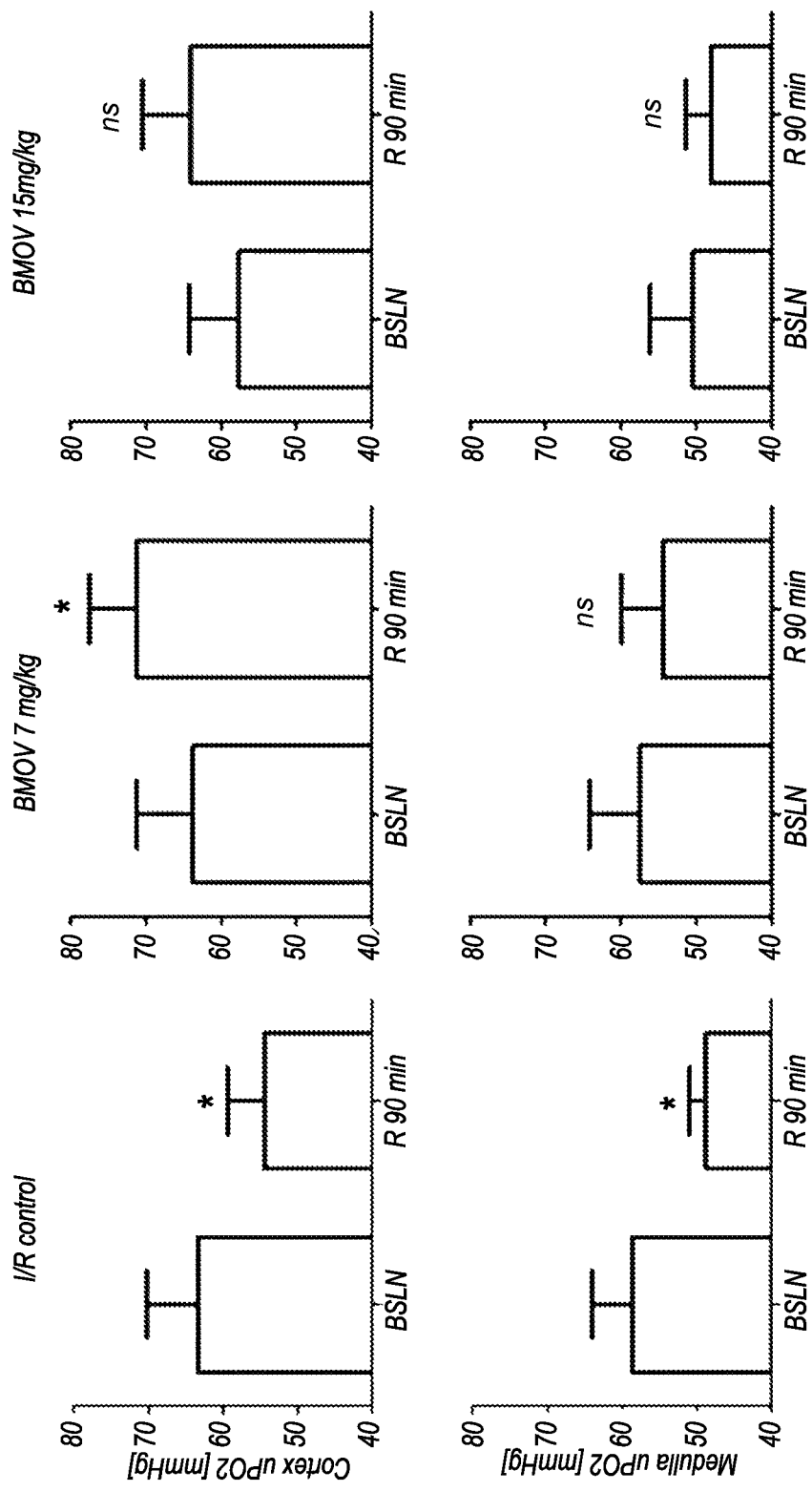
FIG. 3 shows renal microvascular oxygen tension ($\mu PO_2$) in the cortex (upper row) and medulla (lower row) at baseline (BSLN) and after 30 min of ischemia and 90 min of reperfusion (R 90 min).

As appears from FIG. 3, BMOV significantly increased microvascular oxygenation (FIG. 3 shows renal microvascular oxygen tension ($\mu PO_2$) in the cortex (upper row) and medulla (lower row) at baseline (BSLN) and after 30 min of ischemia and 90 min of reperfusion (R 90 min). nsp>0.05 (not significant), *p<0.05, p<0.01, and *p<0.001 vs BSLN).

Renal Function

The data show that renal oxygen consumption and creatinine clearance were not affected by I/R injury, but the amount of oxygen required for sodium reabsorption ($VO_2$/Tna+) was increased, indicating reduced renal oxygen utilization efficiency. The data also show that BMOV increased renal oxygen utilization efficiency and that the effects of BMOV were not dose-dependent.

Figure 4:
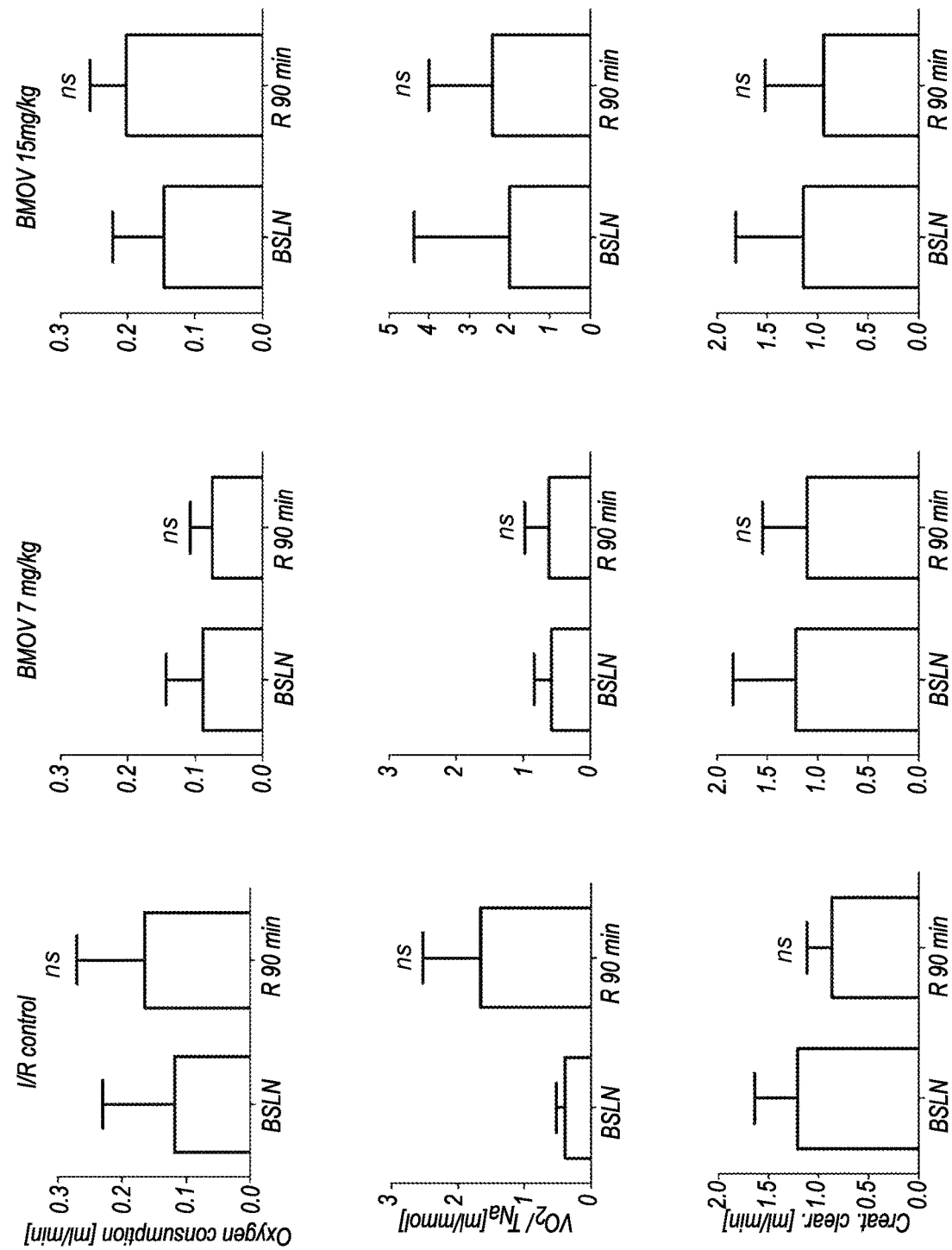
FIG. 4 shows renal oxygen consumption (upper row), the amount of oxygen required for sodium reabsorption (VO2/Tna+) (middle row), and creatinine clearance (creat. clear.) (lower row) at baseline (BSLN) and after 30 min of ischemia and 90 min of reperfusion (R 90 min).

FIG. 4 shows that BMOV increased renal oxygen utilization efficiency (FIG. 4 shows renal oxygen consumption (upper row), the amount of oxygen required for sodium reabsorption (VO2/Tna+) (middle row), and creatinine clearance (creat. clear.) (lower row) at baseline (BSLN) and after 30 min of ischemia and 90 min of reperfusion (R 90 min). $nsp>0.05$ (not significant), $*p<0.05$, $p<0.01$, and $*p<0.001$ vs BSLN).

Figure 5:
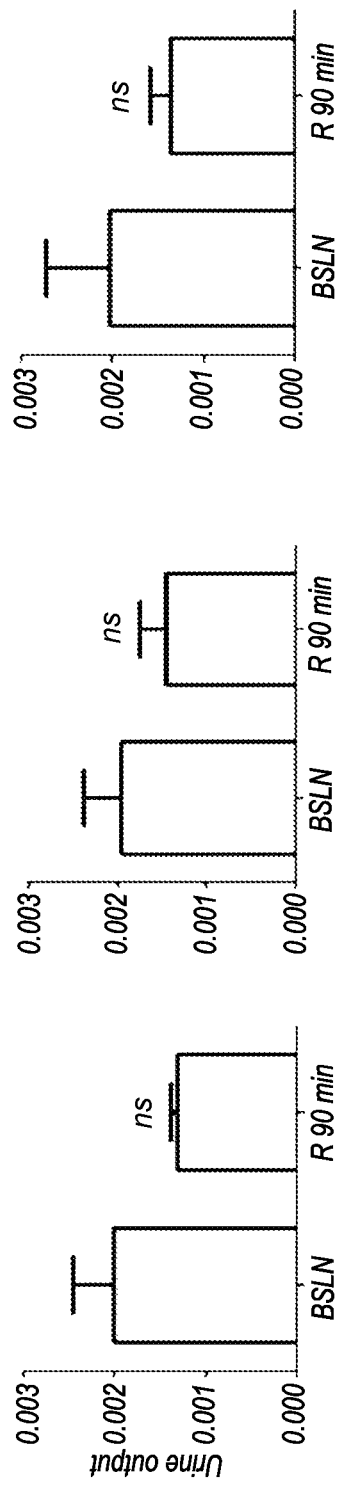
FIG. 5 shows urine output at baseline (BSLN) and after 30 min of ischemia and 90 min of reperfusion (R 90 min).

FIG. 5 shows urine output at baseline (BSLN) and after 30 min of ischemia and 90 min of reperfusion (R 90 min). $nsp>0.05$ (not significant).

Biomarkers of Inflammation Activation

The data also show that I/R injury led to inflammatory activation. The data further show that BMOV significantly decreased inflammatory activation and that the effects of BMOV were dose-dependent, i.e., the iNOS expression was significantly lower in the group treated with the high dose BMOV compared to the levels in the group treated with the low dose.

Figure 6:
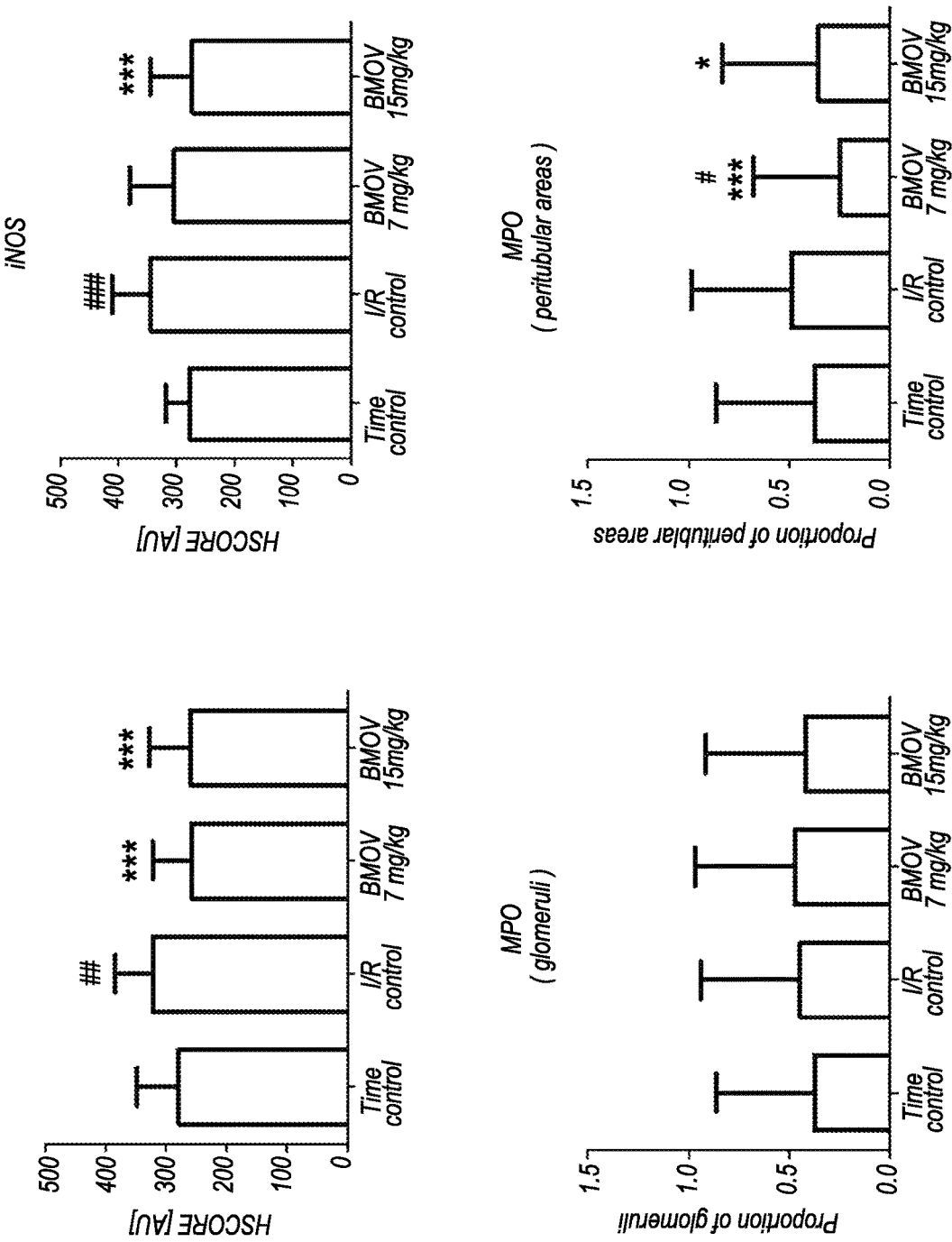
FIG. 6 shows IL-6 and iNOS expression (upper row) and MPO-stained leukocyte appearance (lower row) after 30 min of ischemia and 90 min of reperfusion (R 90 min).

As appears from FIG. 6, BMOV significantly decreased inflammatory activation (FIG. 6 shows IL-6 and iNOS expression (upper row) and MPO-stained leukocyte appearance (lower row) after 30 min of ischemia and 90 min of reperfusion (R 90 min). $nsp>0.05$ (not significant), $*p<0.05$, $p<0.01$, and $*p<0.001$ vs I/R control).

Biomarkers of Renal Injury

Figure 7:
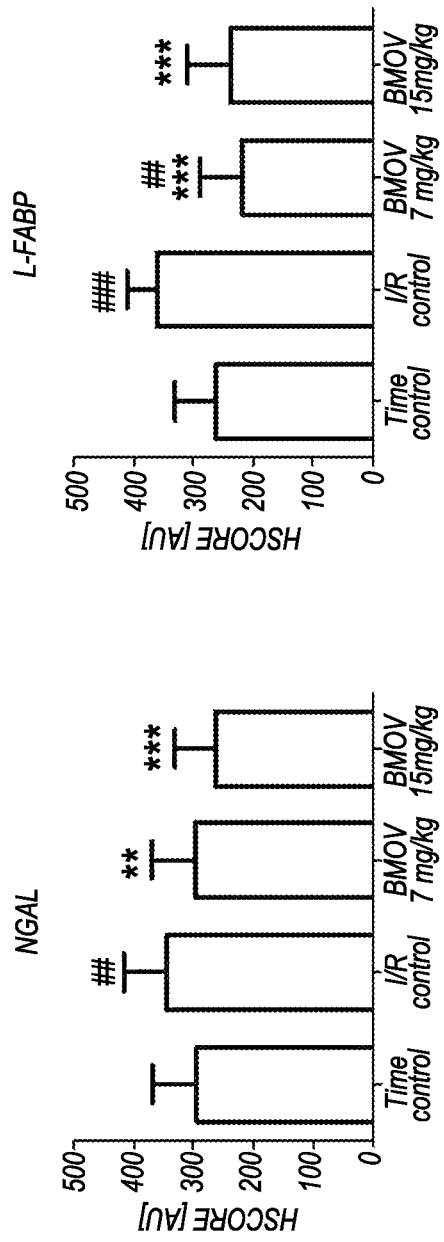
FIG. 7 shows IL-6 and iNOS expression (upper row) and MPO-stained leukocyte appearance (lower row) after 30 min of ischemia and 90 min of reperfusion (R 90 min).

The data show that I/R led to renal injury. The data also show that BMOV significantly decreased renal injury and that the effects of BMOV were dose-dependent, i.e., the NGAL levels were significantly lower in the group treated with the high dose BMOV compared to the levels in the group treated with the low dose. As appears from FIG. 7, BMOV significantly decreased renal injury (FIG. 7 shows IL-6 and iNOS expression (upper row) and MPO-stained leukocyte appearance (lower row) after 30 min of ischemia and 90 min of reperfusion (R 90 min). $nsp>0.05$ (not significant), $*p<0.05$, $p<0.01$, and $*p<0.001$ vs FR control and $+p<0.05$ vs BMOV 7 mg/kg).

Conclusions

Renal I/R led to:
1) decreased mean arterial pressure;
2) decreased renal blood flow and oxygen delivery;
3) decreased microvascular oxygenation in the renal cortex and medulla;
4) decreased renal oxygen utilization efficiency;
5) inflammatory activation; and
6) renal injury.

BMOV did not affect:
1) mean arterial pressure; and
2) renal hemodynamics and oxygen delivery.

BMOV did:
1) increase microvascular oxygenation;
2) increase renal oxygen utilization efficiency
3) decrease inflammatory activation; and
4) decrease renal injury.

The invention claimed is:

1. A method for maintaining normoglycemia in a non-diabetic patient suffering from acute renal failure (ARF), acute renal insufficiency (ACI), or both, comprising parenterally administering to the patient a pharmaceutical composition comprising an effective amount of bis(maltolato)oxovanadium(IV) (BMOV) as the sole active ingredient an wherein blood glucose levels are maintained between 80 and about 110 mg/dl.

2. The method according to claim 1, wherein the ARF and/or ACI is induced by an injury, an insult, a trauma, a medical treatment, an infection, a stroke, coronary bypass surgery or a treatment of myocardial infarction.

3. The method according to claim 1, wherein the pharmaceutical composition is administered intravenously.

4. The method according to claim 1, wherein the administration is carried out for one to seven days.

5. The method according to claim 1, wherein the patient is hospitalized in an intensive care unit (ICU).

6. The method according to claim 1, further comprising co-administering a nutritional supplement to the patient.

7. The method according to claim 6, wherein the nutritional supplement is selected from the group consisting of magnesium, fish oil, potassium, copper, selenium, vitamin D, vitamin E, chromium and mixtures thereof.

8. The method according to claim 1, wherein the patient suffers from acute renal insufficiency (ACI).

9. A method for preventing or limiting renal ischemia-reperfusion (I/R) in a non-diabetic patient suffering from acute renal failure (ARF), acute renal insufficiency (ACI), or both, comprising parenterally administering to the patient a pharmaceutical composition comprising an effective amount of bis(maltolato)oxovanadium(IV) (BMOV) as the sole active ingredient.

10. The method according to claim 9, wherein the renal ischemia-reperfusion (I/R) causes one or more adverse effects selected from the group consisting of reperfusion injury, renal hypoxia, oxidative stress, irreversible damage with organ failure, reduced microvascular oxygenation, reduced renal oxygen utilization, increased inflammation activation and, increased renal injury.

11. The method according to claim 1, wherein the patient suffers from acute renal failure (ARF).

* * * * *